United States Patent [19]

Duffett

[11] Patent Number: Plant 5,350

[45] Date of Patent: Nov. 20, 1984

[54] CHRYSANTHEMUM PLANT NAMED TRUE LUV

[75] Inventor: William E. Duffett, Salinas, Calif.

[73] Assignee: Yoder Brothers, Inc., Barberton, Ohio

[21] Appl. No.: 473,565

[22] Filed: Mar. 9, 1983

[51] Int. Cl.[3] ..... A01H 5/00

[52] U.S. Cl. ..... Plt./76

[58] Field of Search ..... Plt./76

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named True Luv having flat capitulum form; decorative capitulum type; deep lavender ray floret color; diameter across face of capitulum ranging from 105 to 115 mm. at maturity; uniform eight week photoperiodic flowering response to short days; short plant height when grown as a pinched disbud pot mum, and semi-spreading branching pattern.

3 Drawing Figures

The present invention comprises a new and distinct cultivar of *Chrysanthemum morifolium,* Ramat., named True Luv.

True Luv is a product of a planned sport induction program which had the objective of creating new chrysanthemum cultivars that would expand the color range on existing cultivars while retaining their other original traits.

True Luv was discovered and selected by William E. Duffett in May 1980 in a controlled environment in Salinas, Calif. as one flowering plant, a color variant within a flowering block established as rooted cuttings from stock plants which had been exposed as unrooted cuttings to an X-ray source of 1800 rads. The irradiated variety was Luv, disclosed in U.S. Plant Pat. No. 4,960 and originated by the present inventor.

The first act of asexual reproduction of True Luv was accomplished when vegetative cuttings were taken from the initial selection in July 1980 in a controlled environment in Salinas, Calif. by a technician working under formulations established and supervised by William E. Duffett. Horticultural examination of selected units initiated November 1981 has demonstrated that the combination of characteristics as herein disclosed for True Luv are firmly fixed and are retained through successive generations of asexual reproduction.

True Luv has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of True Luv which in combination distinguish this chrysanthemum as a new and distinct cultivar:

(1) Flat capitulum form;

(2) Decorative capitulum type;

(3) Deep lavender ray floret color;

(4) Diameter across face of capitulum ranging from 105 to 115 mm. at maturity;

(5) Uniform eight week photoperiodic flowering response to short days;

(6) Short plant height, requiring 2–3 long day weeks prior to pinch and short days, and 0–1 application of 2500 ppm B-9 after the beginning of short days of attain a flowered plant height of 20 to 30 cm., and (7) Semi-spreading branching pattern.

The accompanying photographic drawings depict typical foliage and inflorescence characteristics of True Luv. Sheet 1 is a color photograph of True Luv grown as a pinched, disbud pot mum, with colors being as accurate as possible with renditions of this type. Sheet 2 is a black and white photograph of three views of the inflorescence of True Luv. Sheet 3 shows the leaves of True Luv in three stages of development (mature, intermediate and immature).

Of the many commercial cultivars known to the present inventor, the most similar in comparison to True Luv is Royal Trophy, disclosed in U.S. Plant Pat. No. 3,549. Reference is made to attached Chart A which compares certain characteristics of True Luv to those same characteristics of Royal Trophy.

True Luv and Royal Trophy are similar in many respects. True Luv differs from Royal Trophy in that it has a more rapid flowering response (8 weeks vs. 9 weeks), a more spreading, branching pattern, and a shorter plant height.

In the following description, color references are made to The Royal Horticultural Society Colour Chart. The color values were determined between 2:30 P.M. and 3:00 P.M. on Aug. 13, 1982 under 150 foot-candle light intensity at Salinas, Calif.

CLASSIFICATION

Botanical: *Chrysanthemum morifolium,* Ramat., cv True Luv.

Commercial: Decorative disbud pot mum.

INFLORESCENCE

Capitulum:

*Form.*—Flat.

*Type.*—Decorative.

*Diameter across face.*—105 To 115 mm.

Corolla of ray florets:

*Color (general tonality from a distance of three meters).*—Deep lavender.

*Color (abaxial).*—74B, 74C.

*Color (adaxial).*—77D.

*Shape.*—Oblong. Rounded tip. Sometimes notched.

Corolla of disc florets:

*Color (mature).*—196D.

*Color (immature).*—144D.

Reproductive organs:

*Androecium.*—Present disc florets only; very few; scant pollen.

*Gynoecium.*—Present both ray and disc florets.

PLANT

General appearance:

*Height.*—Short; 20 to 30 cm. given 2 long day weeks before pinch and lights out, and 0–1 applications of 2500 ppm B-9 SP after lights out.

*Branching pattern.*—Semi-spreading.

Foliage:

*Color (abaxial).*—147A.

*Color (adaxial).*—147B.

*Shape.*—Deeply lobed. Moderately serrated.

CHART A

COMPARISON OF TRUE LUV AND ROYAL TROPHY

| CULTIVAR | RAY FLORET COLOR | CAPITULUM FORM AND TYPE | BRANCHING PATTERN |
|---|---|---|---|
| TRUE LUV | DEEP LAVENDER | FLAT DECORATIVE | SEMI-SPREADING |
| ROYAL TROPHY | DEEP LAVENDER | FLAT DECORATIVE | SEMI-SPREADING |

CHART A-continued

COMPARISON OF TRUE LUV AND ROYAL TROPHY

| CULTIVAR | DIAMETER ACROSS FACE OF CAPITULUM | PLANT HEIGHT | FLOWERING RESPONSE PERIOD |
|---|---|---|---|
| TRUE LUV | 105 to 115 mm. | SHORT 20 to 30 cm. | 8 WEEKS |
| ROYAL TROPHY U.S. Plant Pat. No. 3,549 | 100 to 115 mm. | SHORT 25 to 35 cm. | 9 WEEKS |

COMPARISONS MADE OF PLANTS GROWN AS PINCHED DISBUD POT MUMS IN SALINAS, CALIFORNIA AND LEAMINGTON, CANADA

I claim:

1. A new and distinct cultivar of *Chrysanthemum morifolium,* Ramat., named True Luv, as described and illustrated, and particularly charcterized as to uniqueness by the combined characteristics of flat capitulum form; decorative capitulum type; deep lavender ray floret color; diameter across face of capitulum ranging from 105 to 115 mm. at maturity; uniform eight week photoperiodic flowering response; short plant height and semi-spreading branching pattern.

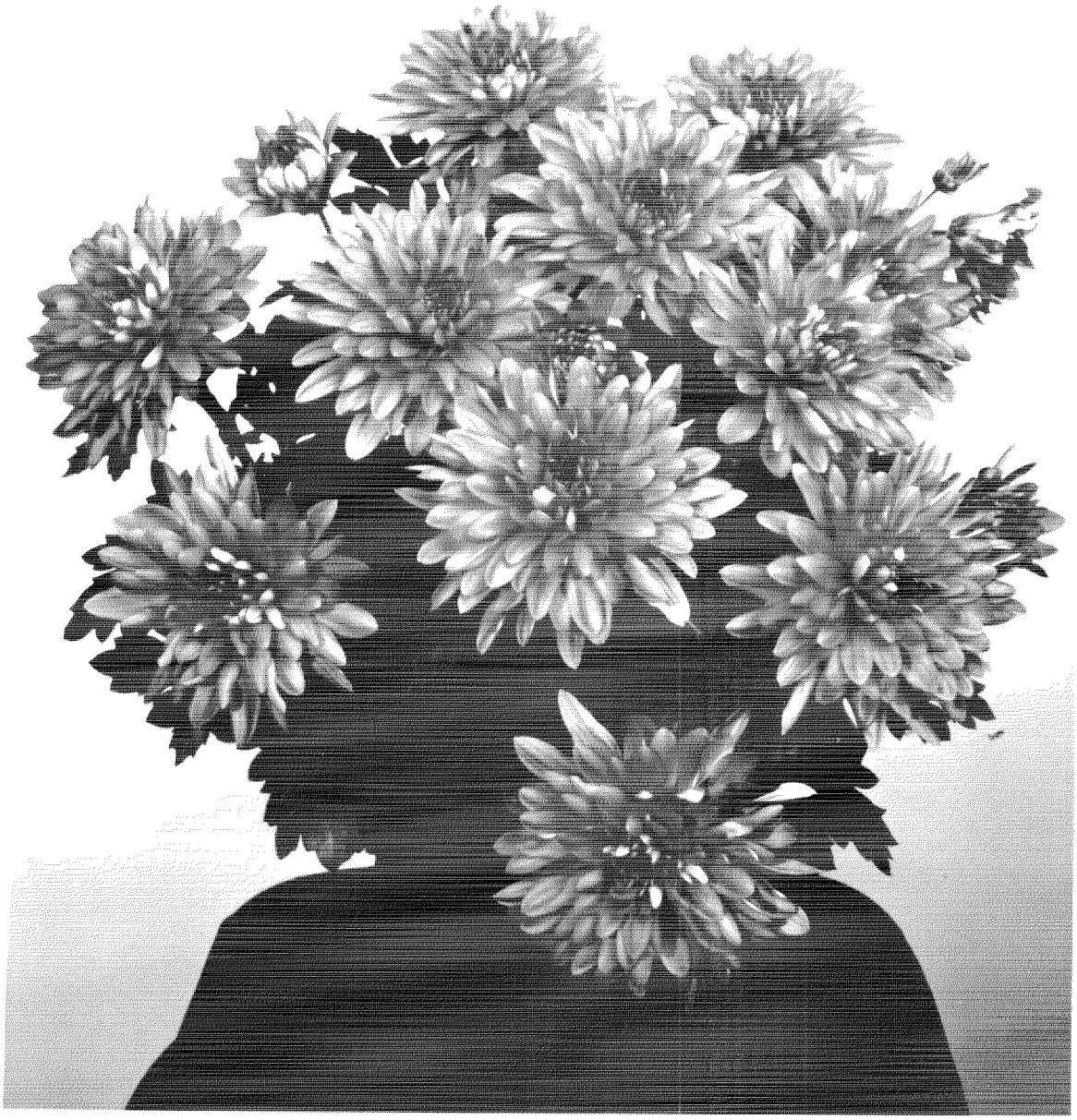

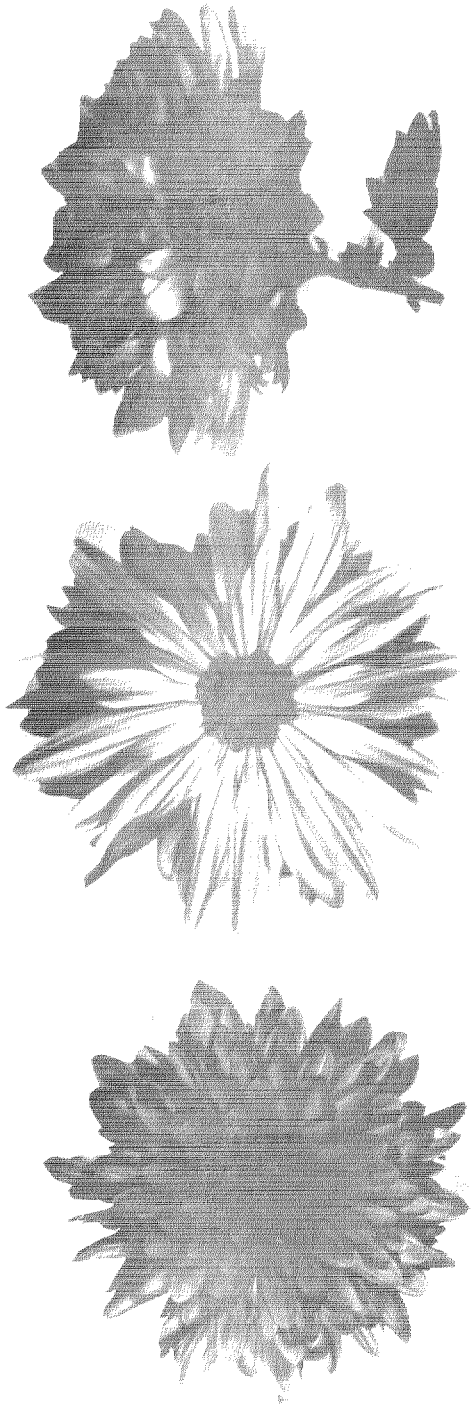

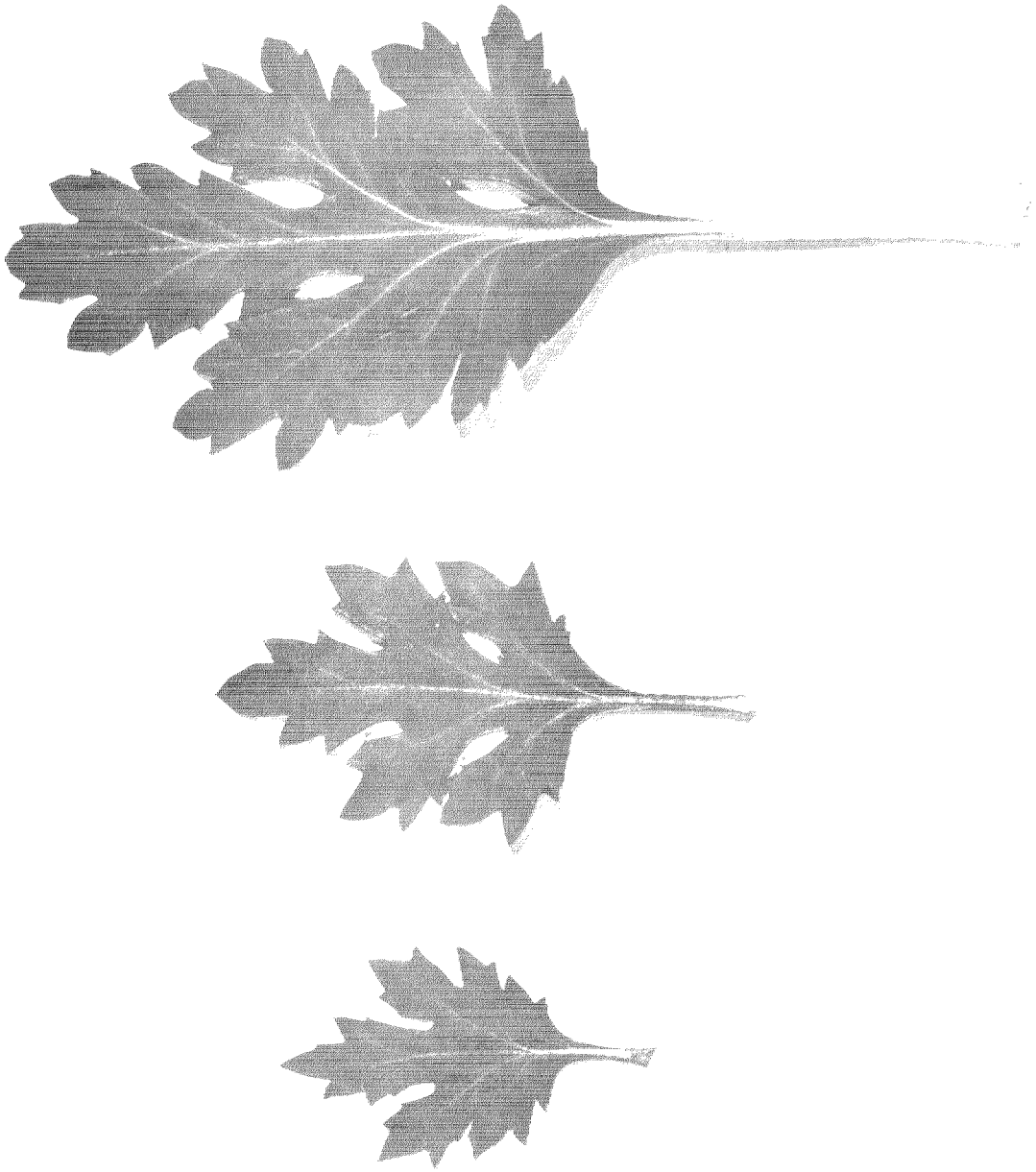

* * * * *